United States Patent
Polyak et al.

[11] Patent Number: 6,056,687
[45] Date of Patent: May 2, 2000

[54] DEVICE FOR ALLEVIATING URINARY INCONTINENCE

[75] Inventors: Mark Polyak, Minnetonka; Sidney F. Hauschild, Bloomington, both of Minn.

[73] Assignee: American Medical Systems, Inc., Minnetonka, Minn.

[21] Appl. No.: 08/984,976

[22] Filed: Dec. 4, 1997

[51] Int. Cl.[7] ........................................................ A61F 2/00
[52] U.S. Cl. ................................ 600/29; 128/DIG. 25; 128/885
[58] Field of Search ............................ 128/DIG. 25, 885; 600/29, 32

[56] References Cited

U.S. PATENT DOCUMENTS

| | | |
|---|---|---|
| 2,510,766 | 6/1950 | Surface . |
| 3,547,401 | 12/1970 | Gurnee et al. . |
| 3,758,073 | 9/1973 | Schulte . |
| 3,841,304 | 10/1974 | Jones . |
| 4,210,132 | 7/1980 | Perlin . |
| 4,344,434 | 8/1982 | Robertson . |
| 4,552,128 | 11/1985 | Haber . |
| 4,587,954 | 5/1986 | Haber . |
| 4,631,062 | 12/1986 | Lassen et al. . |
| 4,690,677 | 9/1987 | Erb . |
| 4,822,333 | 4/1989 | Lavarenne . |
| 4,850,953 | 7/1989 | Haber et al. ...................... 128/DIG. 25 |
| 4,968,294 | 11/1990 | Salama . |
| 5,074,855 | 12/1991 | Rosenbluth et al. . |
| 5,082,006 | 1/1992 | Jonasson . |
| 5,114,398 | 5/1992 | Trick et al. . |
| 5,140,999 | 8/1992 | Ardito . |
| 5,336,208 | 8/1994 | Rosenbluth et al. . |
| 5,352,182 | 10/1994 | Kalb et al. . |
| 5,483,976 | 1/1996 | McLaughlin et al. . |
| 5,640,976 | 6/1997 | Levius . |
| 5,662,582 | 9/1997 | Levius et al. . |
| 5,711,314 | 1/1998 | Ardito . |
| 5,722,931 | 3/1998 | Heaven . |
| 5,752,525 | 5/1998 | Simon et al. ............................. 600/29 |
| 5,755,236 | 5/1998 | Dann et al. . |
| 5,813,974 | 9/1998 | Guardia . |

FOREIGN PATENT DOCUMENTS

| | | |
|---|---|---|
| 0535778 B1 | 7/1995 | European Pat. Off. . |
| 0780105 A2 | 6/1997 | European Pat. Off. . |
| WO 92/06731 | 4/1992 | WIPO . |
| WO 92/11826 | 7/1992 | WIPO . |
| WO 92/19192 | 11/1992 | WIPO . |
| WO 93/08765 | 5/1993 | WIPO . |
| WO 94/26915 | 11/1994 | WIPO . |
| WO 95/08968 | 4/1995 | WIPO . |
| WO 96/26688 | 9/1996 | WIPO . |
| WO 96/39096 | 12/1996 | WIPO . |
| WO 96/39989 | 12/1996 | WIPO . |
| WO 96/39990 | 12/1996 | WIPO . |
| WO 96/39991 | 12/1996 | WIPO . |
| WO 97/06758 | 2/1997 | WIPO . |
| WO 97/17909 | 5/1997 | WIPO . |
| WO 97/25947 | 7/1997 | WIPO . |
| WO 98/19640 | 5/1998 | WIPO . |
| WO 98/2555 | 6/1998 | WIPO . |

*Primary Examiner*—Linda C. M. Dvorak
*Assistant Examiner*—R Kearney
*Attorney, Agent, or Firm*—Oppenheimer Wolff & Donnelly, LLP

[57] ABSTRACT

A device for treating leakage from an external orifice in the body of a patient which comprises a first member having a body-contacting first surface and an opposing second surface about an aperture, which first surface is attachable to the patient with said aperture positioned over said orifice, and a second member integral with said second surface, which second member comprises a valve mounted over said aperture, which valve has a closed position which prevents leakage of fluid through the device and an open position which allows fluid to flow through said aperture when desired, the closed and open positions being achievable without removing the device from the body of the patient.

29 Claims, 4 Drawing Sheets

DEVICE FOR ALLEVIATING URINARY INCONTINENCE

FIELD OF INVENTION

This invention relates to a device for alleviating urinary incontinence. More particularly, the invention is concerned with a device which facilitates control of urination by preventing undesirable leakage of urine and yet allowing micturition when required without removal of the device from the body of the patient. A most preferred embodiment of the device is for alleviating urinary incontinence, particularly stress incontinence, in a female patient. An embodiment for use with a male patient is also included. A further embodiment for dealing with leakage from a body stoma is also contemplated.

BACKGROUND OF THE INVENTION

Urinary incontinence, which is a condition involving involuntary loss of urine, is a problem with very many patients, particularly female patients, throughout the world. Sometimes the problem is treated with surgery. However, when the patient can not receive surgery or suffers only from a partial loss of urine, the problem may be treated non-surgically by use of an internal (intra-urethral or intra-vaginal) or external device. A number of external female devices have been proposed in the art.

For example, U.S. Pat. No. 5,074,855 discloses a device for controlling urinary incontinence in a human female comprising a resilient pad configured to seal against and occlude the urethral meatus of the user. A similar device is disclosed in U.S. Pat. No. 5,336,208. In both these devices, an adhesive is provided to seal the body of the device against the urethral meatus.

International Applications Nos. 96/39989, 96/39990 and 96/39991 each disclose a female urinary incontinence device in the form of a urethral cap with a partially deformable body portion, a hand gripping portion and a body contacting surface. The body portion defines a chamber which allows for a vacuum seal when applied to the patient's body.

Each of the above devices prevents urinary leakage by occluding the external urethral orifice and each has to be removed by the patient to allow micturition.

It is desirable to have a device which satisfactorily prevents leakage and also facilitates micturition without the need to remove the device from the body of the patient. It has now been found that these desiridata may be achieved by a device which incorporates an easily operable valve which prevents leakage when closed and allows flow when open.

SUMMARY OF THE INVENTION

According to the invention there is provided a device for treating leakage from an external orifice in the body of a patient, which device comprises a first member having a body-contacting first surface and an opposing second surface about an aperture, which first surface is attachable to the body of the patient with said aperture positioned over said orifice, and a second member integral with said second surface, which second member comprises a valve mounted over said aperture, which valve has a closed position which prevents leakage of fluid through the device and an open position which allows fluid from said orifice to flow through said aperture when desired, the closed and open positions being achievable without removing the device from the body of the patient.

When the external orifice is a urethral orifice the fluid is urine and accordingly the invention provides, as a preferred embodiment, a device for alleviating urinary incontinence in a patient having an external urethral orifice, which device comprises a first member having a body-contacting first surface and an opposing second surface about an aperture, which first surface is attachable to the patient with said aperture positioned over said urethral orifice, and a second member integral with said second surface, which second member comprises a valve mounted over said aperture, which valve has a closed position which prevents leakage of urine through the device and an open position which allows urine from said urethral orifice to flow through said aperture upon micturition, the closed and open positions being achievable without removing the device from the patient.

In a further preferred embodiment at least a portion of said first surface is coated with a biologically-compatible adhesive, i.e. a medical adhesive, to facilitate attachment of the surface to the body, e.g. the floor of the labial vestibule around the urethral meatus, of the patient.

A particularly preferred embodiment of the invention is a device as described above for alleviating urinary incontinence in a female patient, in which said first member is a substantially circular or oval shaped flange having a first surface at least a portion of which is coated with a biologically-compatible adhesive so that said first surface is attachable to the floor of the labial vestibule, and said valve is defined by a foldable extension of the flange, which extension forms two foldable flaps having a closed position wherein the flaps are folded inwardly to form a closure over the aperture and an open position wherein the flaps extend outwardly to define a flow path from the aperture to the exterior.

The valve of the invention may have any one of a number of different configurations.

In each preferred version of the valve, the aperture is preferably funnel-shaped and the wall of the funnel is defined by the first surface of the flange. However, the positioning of the portions of the flange which act upon the foldable flaps to effect closure of the valve, each of which is herein designated as a "pincher", relative to the other portions, differs in the various versions. The configuration of the portions which make up the valve and the foldable flaps thereof and the spatial relationship of these portions with respect to each other is described in detail hereinafter with reference to the embodiments illustrated in the accompanying drawings.

Each foldable flap of the valve is preferably made of a material which is sufficiently elastic to be folded and compressed or pinched a number of times without deterioration and the preferred material is a biologically compatible elastomer. Typically all components of the device are integral with each other and are made from the same elastomeric material.

A device suitable for a male patient is also included within the invention, and in this embodiment the first member will have the shape of a short condom instead of a flange.

Additionally the invention also encompasses an embodiment which may be used to control leakage from a body stoma and allow drainage therefrom when desired. The components of such an embodiment are analogous to those of the herein described embodiments for alleviating urinary incontinence.

BRIEF DESCRIPTION OF DRAWINGS

The device of the invention will be particularly described with reference to preferred embodiments illustrated in the accompanying drawings, in which.

DETAILED DESCRIPTION OF THE INVENTION

Figure 1:
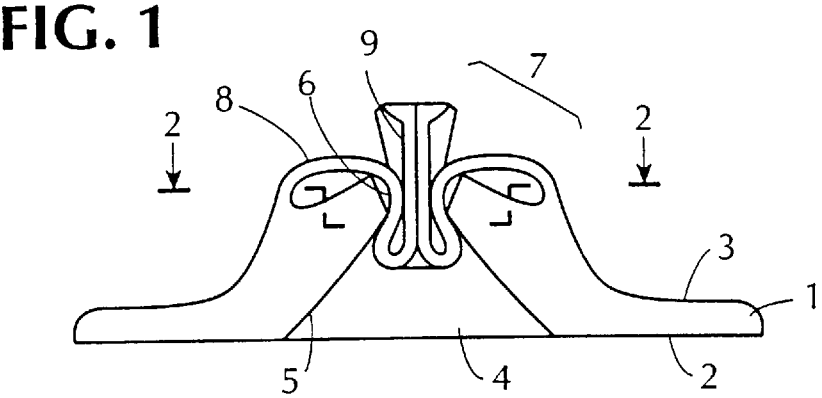
FIG. 1 is a schematic side elevation of a first embodiment of the invention showing the valve in the closed position.
Figure 2:
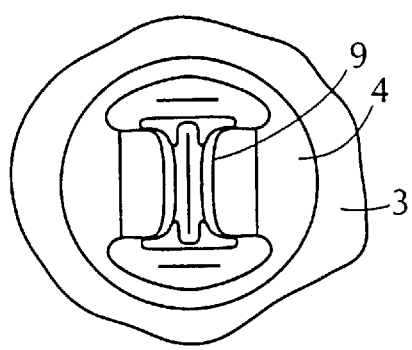
FIG. 2 is a section through line II—II of FIG. 1.

The device illustrated in FIGS. 1–5 of the accompanying drawings is a preferred first embodiment for the alleviation of urinary incontinence in a female patient.

The device comprises a first member 1 having a body-contacting first surface 2 and an opposing second surface 3. In the embodiment illustrated the first member is a substantially circular flange, wherein at least a portion of the first surface 2 is coated with a medical adhesive. Alternatively the first member may have a substantially oval configuration or any other configuration which will facilitate placement over the urethral meatus with the minimum discomfort. The flange defines an aperture 4 which will be positioned over the urethral orifice when the first surface is attached to the patients body with the aid of the adhesive. The aperture has a funnel-shaped wall 5 which narrows to a neck 6 which acts as a pincher to close the valve as described hereinafter.

Figure 3:
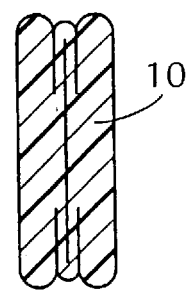
FIG. 3 is a section through the closed duct of the valve.
Figure 4:
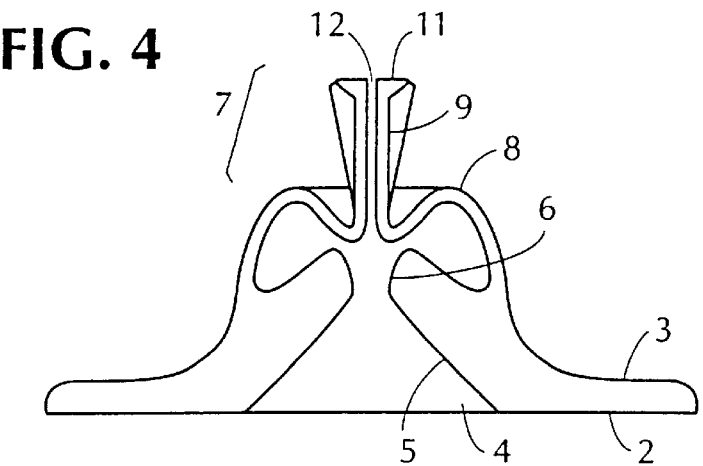
FIG. 4 is a schematic side elevation of the first embodiment showing the valve in the open position.
Figure 5:
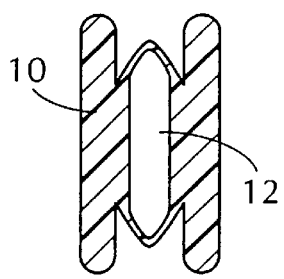
FIG. 5 is a section through the open duct of the valve.

The device further comprises a second member 7 which is a valve mounted over the aperture. The valve is defined by a foldable extension of the flange which comprises two foldable flaps each comprising a dome portion 8 and a duct portion 9. As shown in FIG. 3 and FIG. 4 the duct portion is defined by side walls 10. In the closed position, as shown in FIG. 1, the flaps fold inwardly and the side walls of the duct portion are pinched by the pinchers to close the duct and form a closure which prevents flow of liquid (urine) outwardly through the aperture. Each foldable extension or flap terminates in a grippable end piece 11 which is pushed inwardly by the patient to close the valve as shown in FIG. 1 and may be pulled outwardly to open the valve as shown in FIG. 3. As illustrated in FIG. 3, when the duct portion is pulled outwardly the valve is in the open position and a flow channel or lumen 12 is provided to allow micturition.

Figure 6:
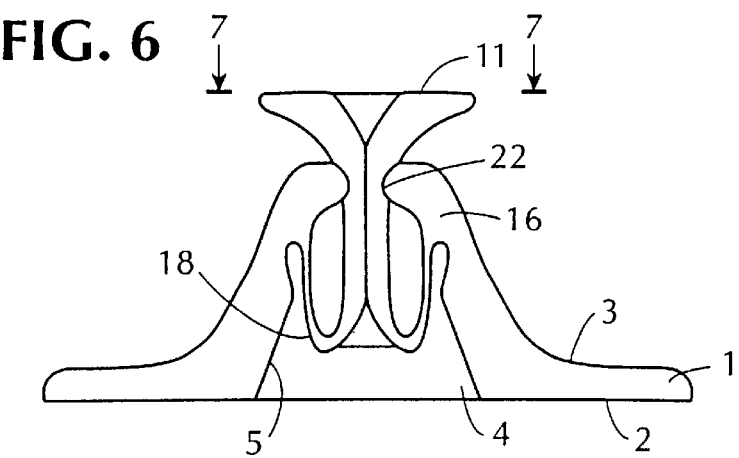
FIG. 6 is a schematic side elevation of a second embodiment of the invention showing the valve in the closed position.
Figure 7:
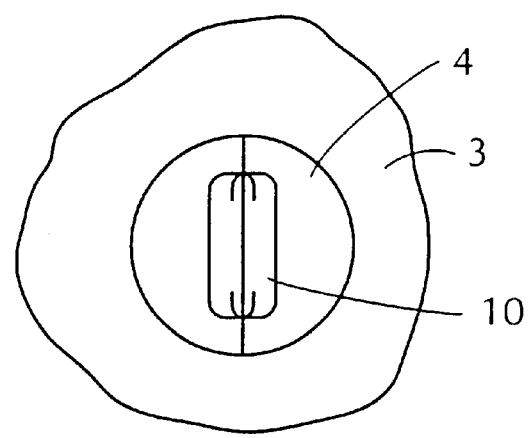
FIG. 7 is a top plan view through line VII of FIG. 6.
Figure 8:
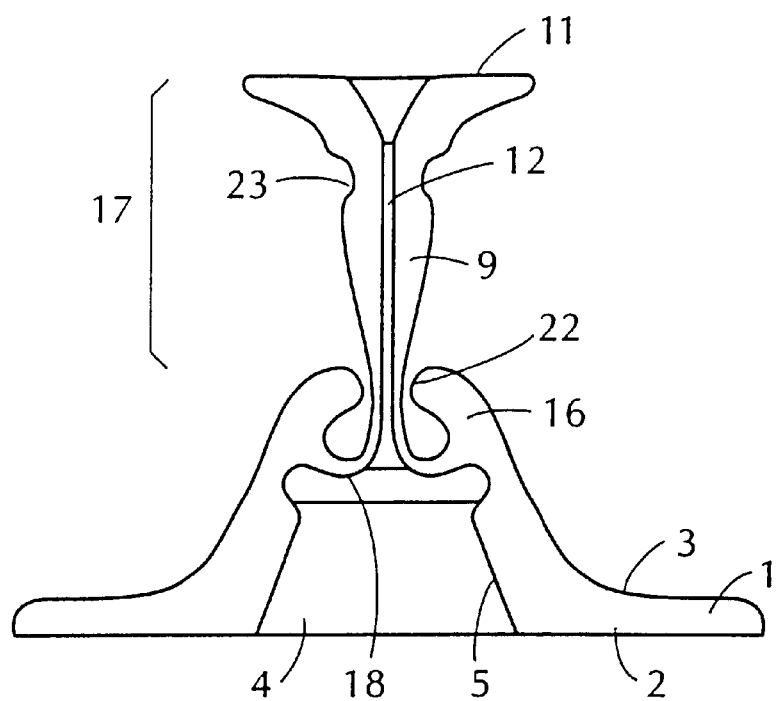
FIG. 8 is a schematic side elevation of the second embodiment showing the valve in the open position.

A second embodiment of the invention is illustrated in FIGS. 6,7 and 8. This embodiment also utilizes a valve defined by foldable flaps, but the configuration thereof differs somewhat from the configuration of FIGS. 1, 2 and 3. In this second embodiment the reference numerals 1, 2, 3, 4, 5, 9, 10, 11 and 12 have analogous meanings to the reference numerals identifying the features of the first embodiment. However, in the second embodiment the configuration of the pinchers 16 and the foldable flaps comprising the valve 17 is somewhat different. Each pincher is still an integral extension of the flange 1, but in the second embodiment each pincher terminates in a snapper 22 which snaps into an indented portion or groove 23 (see FIG. 8) in the side wall 10 of the duct when the valve is closed. The dome 18 of each flap projects within the funnel of the aperture in contrast to the outside configuration of the first embodiment. When the valve is pushed in each snapper snaps into the groove 23 and the combination of snappers and pinchers closes the lumen 12. When the valve is opened as shown in FIG. 8 each snapper is withdrawn from each groove and the lumen opens to allow micturition.

Figure 9:
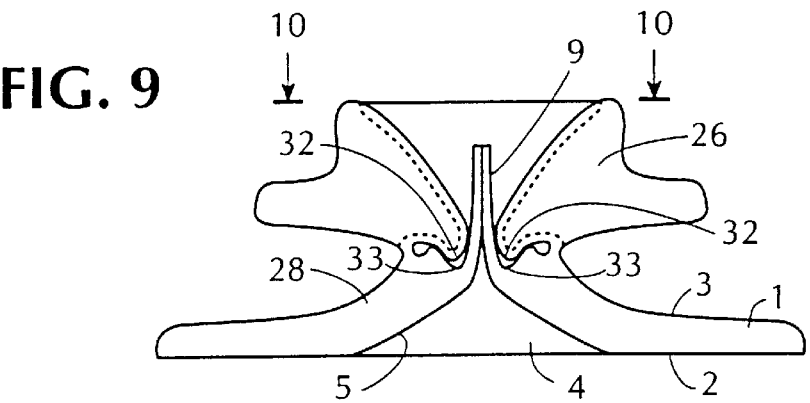
FIG. 9 is a schematic side elevation of a third embodiment of the invention showing the valve in the closed position.
Figure 10:
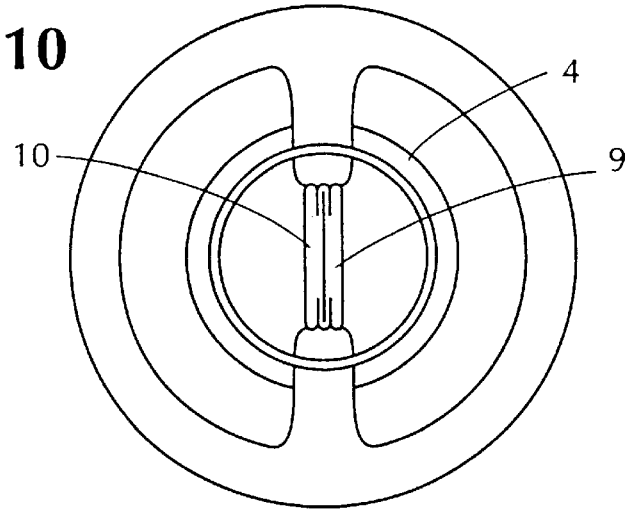
FIG. 10 is a top plan view through line X of FIG. 9.
Figure 11:
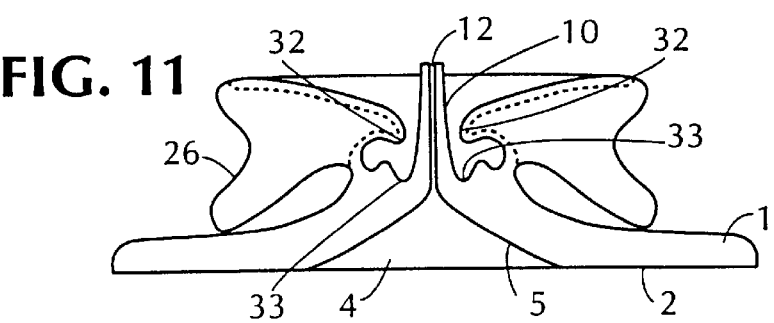
FIG. 11 is a schematic side elevation of the third embodiment showing the valve in the open position.

A further variation of the invention is a third embodiment as illustrated in FIGS. 9, 10 and 11. Here again reference numerals 1, 2, 3, 4, 5, 9, 10 and 12 have analogous meanings to the reference numerals used in the previous figures. However, in the third embodiment the dome 28 has a different profile from that in the first and second embodiments and so has the pincher 26. In the third embodiment each pincher 26 comprises a wing-shaped portion which includes a snapper 32. The closed position of the valve as shown in FIG. 9 is achieved by squeezing the wing portions so that each snapper 32 snaps into a groove 33 in the dome and the pinchers close the duct portion 9. The open position is achieved by pushing the wing portions outwardly.

In each of the above-described embodiments the size of the flange is such that it may be realasably attached to the labial vestibule without discomfort to the patient. The aperture should be large enough so that when it is positioned over the urethral orifice there should be sufficient clearance to facilitate micturition when desired. Typically the flange would have an external diameter of about 2 to 3 cm. depending upon the body size of the patient. The protruding dimension of the device should be no more than 1.5 to 2 cm. between the open and closed positions of the valve.

The incorporation of a valve as described above in a device according to any one of the preferred three embodiments described hereinabove provides a valuable means for the alleviation of urinary incontinence, particularly stress incontinence, in females, which prevents leakage and yet allows micturition when desired, with minimal discomfort and maximal ease of operation. By allowing micturition without the need to remove the device, the patient is provided with a device which is clearly advantageous over the various plugs and pads available heretofore.

The device according to the invention may be worn by the patient for as much as a whole day or even longer if the patient's condition so allows. The preferred device is intended to be disposable.

The device may be made with a type of valve other than valve as described herein; however, valves with a more complex mechanism would be more costly to produce and any valve which involves a complicated opening and closing procedure, particularly a procedure which takes more than a few seconds of time, should be avoided. Furthermore, it is important that operation of the valve should not significantly affect the attachment of the device to the body of the patient. Additionally, the structure described herein may be made in one piece from the same elastomeric material, apart from the adhesive.

Thus, for the reasons of easy operation, ease of manufacture, low cost and disposability, at least, a device incorporating a valve, as herein described, is the preferred embodiment of the invention.

We claim:

1. A device for treating leakage from an external orifice in the body of a patient, which device comprises a first member having a body-contacting first surface and an opposing second surface having an aperture extending between the first and second surfaces, which first surface is attachable to the body of the patient with said aperture positioned over said orifice, and a second member integral with said second surface, which second member comprises a valve mounted over said aperture, said valve is defined by a foldable extension about the aperture from the second surface, which extension folds between a closed position wherein the extension is folded inwardly upon itself to form a closure over the aperture and an open position wherein the extension extends outwardly to define a flow path from the aperture to the exterior, which valve extension has a closed position which prevents leakage of fluid through the device and an open position which allows fluid from said orifice to flow through said aperture when desired, the closed and open positions being achievable without removing the device from the body of the patient.

2. A device for alleviating urinary incontinence in a patient having an external urethral orifice, which device comprises a first member having a body-contacting first surface and an opposing second surface having an aperture extending between the first and second surfaces, which first surface is attachable to the patient with said aperture positioned over said urethral orifice, and a second member integral with said second surface, which second member comprises a valve mounted over said aperture, said valve is defined by a foldable extension about the aperture from the second surface, which extension folds between a closed position wherein the extension is folded inwardly upon itself to form a closure over the aperture and an open position wherein the extension extends outwardly to define a flow path from the aperture to the exterior, which valve extension has a closed position which prevents leakage of urine through the device and an open position which allows urine from said urethral orifice to flow through said aperture upon micturition, the closed and open positions being achievable without removing the device from the patient.

3. A device according to claim 2, in which at least a portion of said first surface is coated with a biologically-compatible adhesive to facilitate attachment of the surface to the body of the patient.

4. A device according to claim 2 for alleviating urinary incontinence in a female patient, in which said first member is a flange having an adhesive-coated first surface which is attachable to the floor of the labial vestibule, and wherein said extension comprises two foldable flaps having a closed position wherein the flaps are folded inwardly to form said closure over the aperture and an open position wherein the flaps extend outwardly to define said flow path from the aperture to the exterior.

5. A device according to claim 4, in which the foldable flaps of the valve are made from a biologically compatible elastomer.

6. A device according to claim 5, in which the flange and flaps are integral with each other and are made from the same elastomer.

7. A device according to claim 4, in which the aperture has a funnel-shaped wall which narrows to a neck having two sides, each of which acts as a pincher to close the valve and the valve is defined by a foldable extension of the flange which comprises two foldable flaps each comprising a dome portion and a duct portion, which duct portion is defined by side walls, wherein the flaps folds inwardly and said side walls are pinched by the pinchers to close the duct and form a closure which prevents flow of urine outwardly through the aperture.

8. A device according to claim 7, in which each foldable flap terminates in a grippable end piece which is pushed inwardly by the patient to close the valve and pulled outwardly to open the valve and provide a flow channel through the duct to allow micturition.

9. A modification of the device according to claim 7, in which each pincher terminates in a snapper which snaps into a groove in the side wall of the duct when the valve is closed and each snapper is withdrawn from each groove to open the valve and allow micturition.

10. A modification of the device according to claim 9, in which each pincher comprises a wing-shaped portion which includes a snapper whereby the closed position of the valve is achieved by squeezing the wing-shaped portions so that each snapper snaps into a groove in the dome portion and the pinchers close the duct portion, and the open position is achieved by pushing the wing portions outwardly.

11. A female urinary incontinence device comprising:
a substantially planar surface having a first side to contact a body of a user during use of said device;
an adhesive applied to said first side of said substantially planar surface, said adhesive having sufficient strength to substantially continuously retain said device to said body for at least one twenty four hour period and through at least one occurrence of user voiding;
an aperture disposed on said substantially planar surface and extending from said first side to a second side of said substantially planar surface; said aperture having a cross-sectional area no smaller than the cross-sectional area of a urethral meatus of a user;
a valve disposed on said second side of said substantially planar surface substantially in alignment with said aperture, said valve being selectively and repeatably actuable by a user between an open position allowing voiding through said aperture and a closed position sealing said aperture from fluid flow; and
a flow channel situated within said valve and substantially in alignment with said aperture, wherein said flow channel comprises deformable walls which seal said flow channel when said valve is in said closed position.

12. A female urinary incontinence device according to claim 11, wherein said valve includes a compressive member urging said deformable walls into a sealing relationship when said valve is in said closed position.

13. A female urinary incontinence device according to claim 12, wherein said compressive member is positioned on said valve such that clearance is present between said compressive member and said deformable walls when said valve is in said open position.

14. A female urinary incontinence device according to claim 11, wherein said deformable walls are movable between a lower position when said valve is in said closed position and a raised position when said valve is in said open position.

15. A female urinary incontinence device according to claim 14, wherein said device has a protruding dimension no greater than about 2 cm when said valve is in said open position.

16. A female urinary incontinence device according to claim 14, wherein a distance between said lower position and said raised position is no greater than about 0.5 cm.

17. A female urinary incontinence device according to claim 11, wherein said valve includes actuator surfaces movable by said user while said device is retained on said body to move said valve into said open position.

18. A female urinary incontinence device comprising:
a substantially planar surface having a first side to contact a body of a user during use of said device;

an adhesive applied to said first side of said substantially planar surface, said adhesive having sufficient strength to substantially continuously retain said device to said body for at least one twenty four hour period and through at least one occurrence of user voiding;

an aperture disposed on said substantially planar surface and extending from said first side to a second side of said substantially planar surface; said aperture having a cross-sectional area no smaller than the cross-sectional area of a urethral meatus of a user;

a valve for controlling fluid flow through said aperture, said valve being selectively actuable between an open and a closed position, said valve being disposed on said second side of said substantially planar surface and said valve being sized sufficiently small such that said valve substantially avoids contact with an undergarment of said user when in said closed position; and a flow channel situated within said valve and substantially in alignment with said aperture, wherein said flow channel comprises deformable walls which seal said flow channel when said valve is in said closed position.

19. A female urinary incontinence device according to claim 18, wherein said valve includes a compressive member urging said deformable walls into a sealing relationship when said valve is in said closed position.

20. A female urinary incontinence device according to claim 19, wherein said compressive member is positioned on said valve such that clearance is present between said compressive member and said deformable walls when said valve is in said open position.

21. A female urinary incontinence device according to claim 19, wherein said deformable walls are movable between a lower position when said valve is in said closed position and a raised position when said valve is in said open position.

22. A female urinary incontinence device according to claim 21, wherein a distance between said lower position and said raised position is no greater than about 0.5 cm.

23. A female urinary incontinence device according to claim 18, wherein said device has a protruding dimension no greater than about 2 cm when said valve is in said open position.

24. A female urinary incontinence device according to claim 18, wherein said valve includes actuator surfaces movable by said user while said device is retained on said body to move said valve into said open position.

25. A method of controlling urinary incontinence comprising:

providing an incontinence device having an aperture with an integral valve for selectively opening and closing said aperture;

fixing by said user of said incontinence device to said user's body such that said aperture is substantially in alignment with the urethral meatus of said user;

opening by said user of said valve to allow voiding by said user through said aperture without removing said device from said body;

closing by said user of said valve to seal said aperture from fluid flow by compressing deformable walls of a flow channel in said valve into a sealing relationship; and, repeating said opening and closing steps as necessary without removing said device from said body.

26. A method according to claim 25, wherein said step of opening includes gripping by the user of actuation surfaces of said valve, which actuation surfaces move said valve between an open and a closed position.

27. A method according to claim 25, wherein said step of opening includes moving said valve in a direction away from said body.

28. A method according to claim 27, wherein said step of opening includes moving said valve in a direction away from said body no greater than about 2 cm from said body.

29. A method according to claim 27, wherein said step of closing includes moving a compressive member into contact with said deformable walls to compress said deformable walls of said flow channel into said sealing relationship.

* * * * *